United States Patent
Ross et al.

(10) Patent No.: US 8,199,000 B2
(45) Date of Patent: Jun. 12, 2012

(54) SYSTEM AND METHOD FOR INTERFERENCE MITIGATION IN A WIRELESS SENSOR NETWORK

(75) Inventors: John Anderson Fergus Ross, Niskayuna, NY (US); David Michael Davenport, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 1293 days.

(21) Appl. No.: 11/862,681

(22) Filed: Sep. 27, 2007

(65) Prior Publication Data

US 2009/0088605 A1  Apr. 2, 2009

(51) Int. Cl.
G08B 21/00 (2006.01)

(52) U.S. Cl. ......... 340/539.12; 340/539.22; 340/539.26; 340/572.1; 600/300; 600/301

(58) Field of Classification Search ............. 340/539.12, 340/539.22, 539.26, 572.1; 600/300, 301
See application file for complete search history.

(56) References Cited

U.S. PATENT DOCUMENTS

| | | | |
|---|---|---|---|
| 5,153,584 A | 10/1992 | Engira | |
| 5,335,664 A | 8/1994 | Nagashima | |
| 5,550,536 A * | 8/1996 | Flaxl | 340/10.3 |
| 5,748,103 A | 5/1998 | Flach et al. | |
| 6,749,566 B2 | 6/2004 | Russ | |
| 6,984,207 B1 | 1/2006 | Sullivan et al. | |
| 6,988,989 B2 | 1/2006 | Weiner et al. | |
| 7,020,508 B2 | 3/2006 | Stivorie et al. | |
| 7,129,836 B2 | 10/2006 | Lawson et al. | |
| 7,609,155 B2 * | 10/2009 | HinKamp | 340/539.12 |
| 2002/0186136 A1 * | 12/2002 | Schuman | 340/573.1 |
| 2003/0162556 A1 | 8/2003 | Libes | |
| 2004/0203381 A1 | 10/2004 | Cahn et al. | |
| 2005/0128104 A1 * | 6/2005 | Karabinis | 340/933 |
| 2005/0206518 A1 | 9/2005 | Welch et al. | |
| 2006/0009697 A1 | 1/2006 | Banet et al. | |
| 2006/0030759 A1 | 2/2006 | Weiner et al. | |
| 2006/0094936 A1 | 5/2006 | Russ | |
| 2006/0155183 A1 | 7/2006 | Kroecker et al. | |
| 2006/0220839 A1 | 10/2006 | Fifolt et al. | |
| 2006/0224048 A1 | 10/2006 | Devaul et al. | |
| 2007/0109117 A1 | 5/2007 | Heitzmann et al. | |
| 2007/0129622 A1 | 6/2007 | Bourget et al. | |
| 2007/0176790 A1 | 8/2007 | Klabunde et al. | |

FOREIGN PATENT DOCUMENTS

| | | |
|---|---|---|
| EP | 1038497 A1 | 9/2000 |
| EP | 1639939 A1 | 3/2006 |
| WO | 2006006158 A1 | 1/2006 |
| WO | 2006008740 A1 | 1/2006 |
| WO | 2006009830 A2 | 1/2006 |
| WO | 2006048840 A1 | 5/2006 |
| WO | 2006050206 A1 | 5/2006 |

(Continued)

*Primary Examiner* — Toan N Pham
*Assistant Examiner* — Mark Rushing
(74) *Attorney, Agent, or Firm* — Marie Claire B. Maple (57) ABSTRACT

A wireless patient monitoring system forms a Network Around a Patient (NAP) and includes sensor nodes configured to acquire patient data from a patient. A gateway device is in bi-directional wireless communication with the sensor nodes for a plurality of defined communication frames. The gateway device is configured to transmit a beacon message to the sensor nodes at each of a plurality of frequencies. The sensor nodes are further configured to receive the beacon message from the gateway device and transmit the acquired patient data to the gateway device at each of the plurality of frequencies.

23 Claims, 4 Drawing Sheets

FOREIGN PATENT DOCUMENTS

| WO | 2006051466 A1 | 5/2006 |
| WO | 2006102538 A2 | 9/2006 |
| WO | 2007014527 A2 | 2/2007 |
| WO | 2007096810 A1 | 8/2007 |

* cited by examiner

SYSTEM AND METHOD FOR INTERFERENCE MITIGATION IN A WIRELESS SENSOR NETWORK

BACKGROUND OF THE INVENTION

The present invention relates generally to wireless sensor networks for system monitoring and, more particularly, to communication schemes between elements of a wireless sensor network.

In sensor monitoring networks employing wireless communications systems, two relevant design issues are data latency and data outage. That is, the time it takes for data to travel from a network of sensors to a readout device (data latency) and the loss of more than a maximum allowable period of data (data outage) are two critical requirements to the performance of a wireless sensor network. In order for a wireless sensor monitoring network to function properly, both data latency and data outage must be within acceptable limits.

To address the issues of reliability and transmission delay, the concept of a beacon controlled sensor network, or so-called time division multiple access (TDMA) approach, has previously been used. In TDMA, various devices use the same transmission frequency channel by dividing a signal into different timeslots within a transmission frame. Signals are transmitted in rapid succession, one after the other, each using its own timeslot, which allows multiple devices to share the same transmission medium (e.g. radio frequency channel) while using only part of its bandwidth.

The use of a TDMA network approach, however, presents a number of challenges. That is, as set forth above, data latency is of great importance in wireless sensor monitoring networks, and thus, a delay in transmission of a packet of data from sensors to a remote receiver to fit within a specific timeslot may not always be feasible, depending on the number of slots present in the frequency channel. Thus, data transmission may be delayed until a subsequent frame.

Additionally, the data outage specifications for a wireless sensor monitoring network may, for example, require a transmission success rate of 95% for signals transmitted from the sensor nodes to the gateway in order to meet the performance requirements. For signals transmitted over a single frequency, such a success rate can be unlikely, as the sensors and the receiver can be in close proximity of an inteferer that occupies the same or adjacent radio frequency spectrum. Signals transmitted on neighboring frequencies may still present significant power within the sensor network's operating frequency, preventing successful message transfer. For example, 802.11b, Bluetooth, Zigbee, 802.15.4 and legacy 802.11 transmitters within a facility will cause problems if these interferers transmit at the same time the wireless sensor monitoring network is transmitting. While previous monitoring networks have implemented the practice of retransmitting a data message multiple times to increase the transmission success rate, such retransmission may cause the data to exceed the delay requirement, greatly reducing the value of the data.

In the context of patient health monitoring, wireless sensor networks may be quite useful, as they may circumvent problems associated with cable clutter and device management. The wireless transfer of data from patient sensors to a gateway device or wireless network allows for the management of such devices to be eased and the burdens associated with cable management to be lessened. However, as described above, the use of wireless sensor networks for patient monitoring requires that communications issues often associated with wireless communication systems be adequately addressed. For patient health monitoring, the issues of data latency and data outage can be extremely problematic. That is, vital sign monitoring (e.g., monitoring of blood pressure, hemoglobin saturation, and features of the electrocardiogram (ECG)) is an important part of patient care since the general or particular health of the patient is determined, in part, through measurement and interpretation of key physiological indicators. Such physiological data, however, is only of use if it is transmitted in a timely and accurate manner. Transmission of such vital sign data must therefore be timely and be transmitted at a high rate of success in order for a wireless patient sensor network to be feasible.

Therefore, it would be desirable to design an apparatus and method that minimizes data latency and data outage. It would also be desirable to design a system and method that allows for timely and reliable data transmission when located in proximity to an inteferer that occupies the same or adjacent radio frequency spectrum. It would also be desirable to design a system which accomplishes this while exchanging a minimum of control messages that contain no data but consume power and frequency resources.

BRIEF DESCRIPTION OF THE INVENTION

The present invention provides a system and method for communication between elements of a wireless patient sensor network that overcomes the aforementioned problems. Data signals between a gateway device and wireless sensors in the wireless patient sensor network are transmitted sequentially at a plural of frequencies via a bi-directional communication link.

In accordance with one aspect of the invention, a wireless patient monitoring system includes a plurality of sensor nodes configured to acquire patient data from a patient and a gateway device in bi-directional wireless communication with the plurality of sensor nodes for a plurality of defined communication frames. The gateway device is configured to transmit a beacon message to the plurality of sensor nodes at each of a plurality of frequencies. The plurality of sensor nodes is further configured to receive the beacon message from the gateway device and transmit the acquired patient data to the gateway device at each of the plurality of frequencies.

In accordance with another aspect of the invention, a method for patient monitoring includes the steps of arranging a plurality of wireless sensors on a patient to acquire health data therefrom and associating the plurality of wireless sensors with a gateway controller by assigning each of the plurality of wireless sensors to a timeslot within the operative frame. The method also includes the steps of transmitting a beacon signal from the gateway controller to the plurality of wireless sensors to activate the wireless sensors during an operative frame and transmitting the health data from the plurality of wireless sensors to the gateway controller via a plurality of data packets during the operative frame in response to the beacon signal. At least one of the beacon signal and the data packets are transmitted over a first frequency channel and a second frequency channel during the operative frame.

In accordance with yet another aspect of the invention, a wireless sensor communications system includes a sensor network configured to acquire system data from a monitored system and a controller positioned in proximity to the sensor network and in wireless communication therewith. Each of the sensor network and the controller are configured to sequentially transmit and receive wireless signals over a first frequency channel (F1) and over a second frequency channel (F2) and switch between the first frequency channel and the second frequency channel at least once during each of a plurality of communication frames, the wireless signals including an activation signal and system data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention provides a system and method for communication between elements of a wireless sensor network. While described herebelow as a wireless patient sensor network comprising a plurality of body worn sensors and a gateway device communicating via the described communications schemes, it is also envisioned that the wireless sensor network is useable in a variety of additional settings. That is, the wireless sensor network of the present invention is also usable in industrial and transportation settings and for sensing and communicating a plurality of different performance parameters associated with mechanical, electrical, and electro-mechanical systems. As such, the following description of a wireless sensor network for use in patient monitoring and the acquisition/transmission of patient data is exemplary only and is only one embodiment of the present invention that is envisioned.

Figure 1:
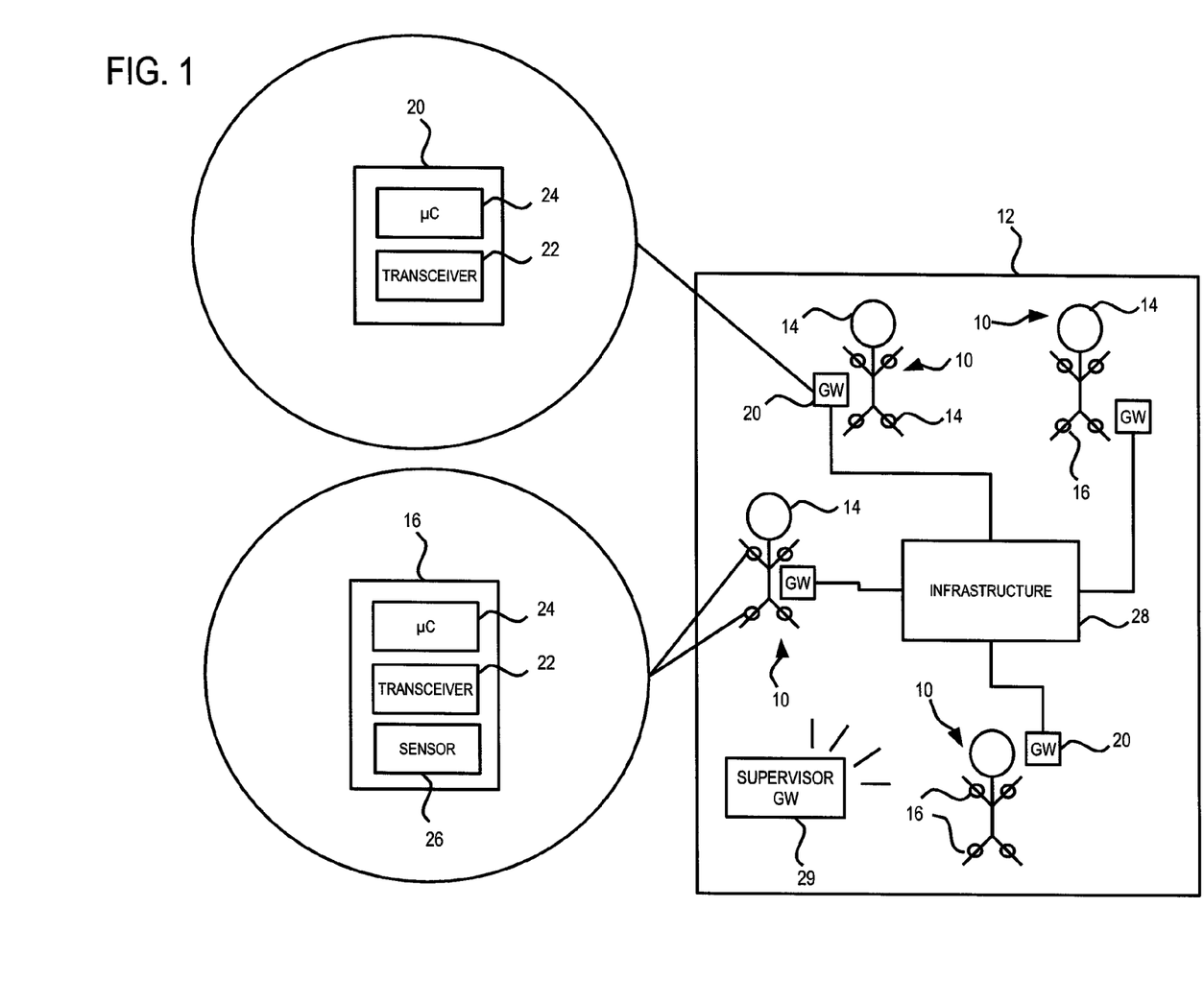
FIG. 1 is a block diagram of a Network Around Patient (NAP) wireless sensor network according to the present invention.

Referring to FIG. 1, a plurality of wireless patient monitoring networks are shown in the form of Networks Around a Patient (NAP) 10. A number of NAPs 10 are shown as present within a healthcare facility 12 for monitoring each of a number of patients 14. Each NAP includes a plurality of wireless, body-worn sensors 16 (i.e., sensor nodes) placed on the patient 14 and forming a sensor network. The wireless sensors 16 are configured as parameter-specific sensor nodes capable of measuring any of a plurality of patient parameters and of combinations thereof. These parameters can include, but are not limited to, physiological parameters such as heart rate, ECG, and blood oxygen saturation. It is also envisioned that wireless sensors 16 be in the form of a sensor device that measures additional patient parameters, such as an accelerometer for measuring patient movement or a photodetector or microphone for measuring ambient light or sound.

The wireless sensors 16 are, in one embodiment, low power, wireless, self-contained sensors that are battery operated; however, it is also envisioned that the type and power characteristics of the sensor can vary. Each of the wireless sensors 16 communicates with, and is in association with, a gateway controller device 20 (i.e., controller) via a bi-directional wireless communication link. The wireless communication link can take the form of several well known communications mediums and, in one embodiment, comprises radio frequency signals. For example, RF signals within a 2.4 GHz ISM band may be used as the medium for the bi-directional wireless communication.

To accommodate bi-directional communication, each of wireless sensors 16 and gateway device 20 includes an integrated circuit transceiver 22. Additionally, the wireless sensors 16 and gateway device 20 also include a micro-controller 24 that allows for the devices to hop/switch between frequencies when transmitting and receiving signals, as will be explained in detail below. Wireless sensors 16 further include a sensing device 26 that measures a specified patient parameter.

As shown in FIG. 1, gateway device 20 is a body-worn device in close proximity to wireless sensors 16, but it is also envisioned that gateway device 20 may also be implemented as a bedside device or other device separate from the patient. Gateway device 20 acts as a wireless bridge that receives data on one or more measured patient parameters and conveys this received patient data (i.e., physiological data, health data) on to a hospital network system or infrastructure 28 using a wired or wireless link. In one embodiment, the patient data is transferred onto the hospital infrastructure 28 from gateway device 20 via a radio frequency allocated specifically for medical telemetry (i.e. WMTS service in the USA); however, other wireless telemetry, wireless LAN, or other radio frequency links may also be used.

While on-body communication within the NAP 10 is bidirectional (i.e., communication between the wireless sensors and the gateway device), one-way communication occurs from the gateway device 20 to the hospital infrastructure 28. Given the one-way link from the gateway 20 to the infrastructure 28, the gateway devices must monitor for interference from other common wireless systems, such as Bluetooth communications devices and the like, and change frequencies accordingly. To facilitate this, one embodiment of NAP includes a supervisor gateway device 29 that is located within the hospital area and sends periodic beacon messages to all gateways 20 in the area. This supervisor gateway 29 conveys frequencies available or used in the vicinity. Supervisor gateway messages occur on a predefined, default channel to which gateways periodically tune for reception. This tiered architecture affords robust mobility of the NAPs 10 as patients roam about the healthcare facility 12.

Figure 2:
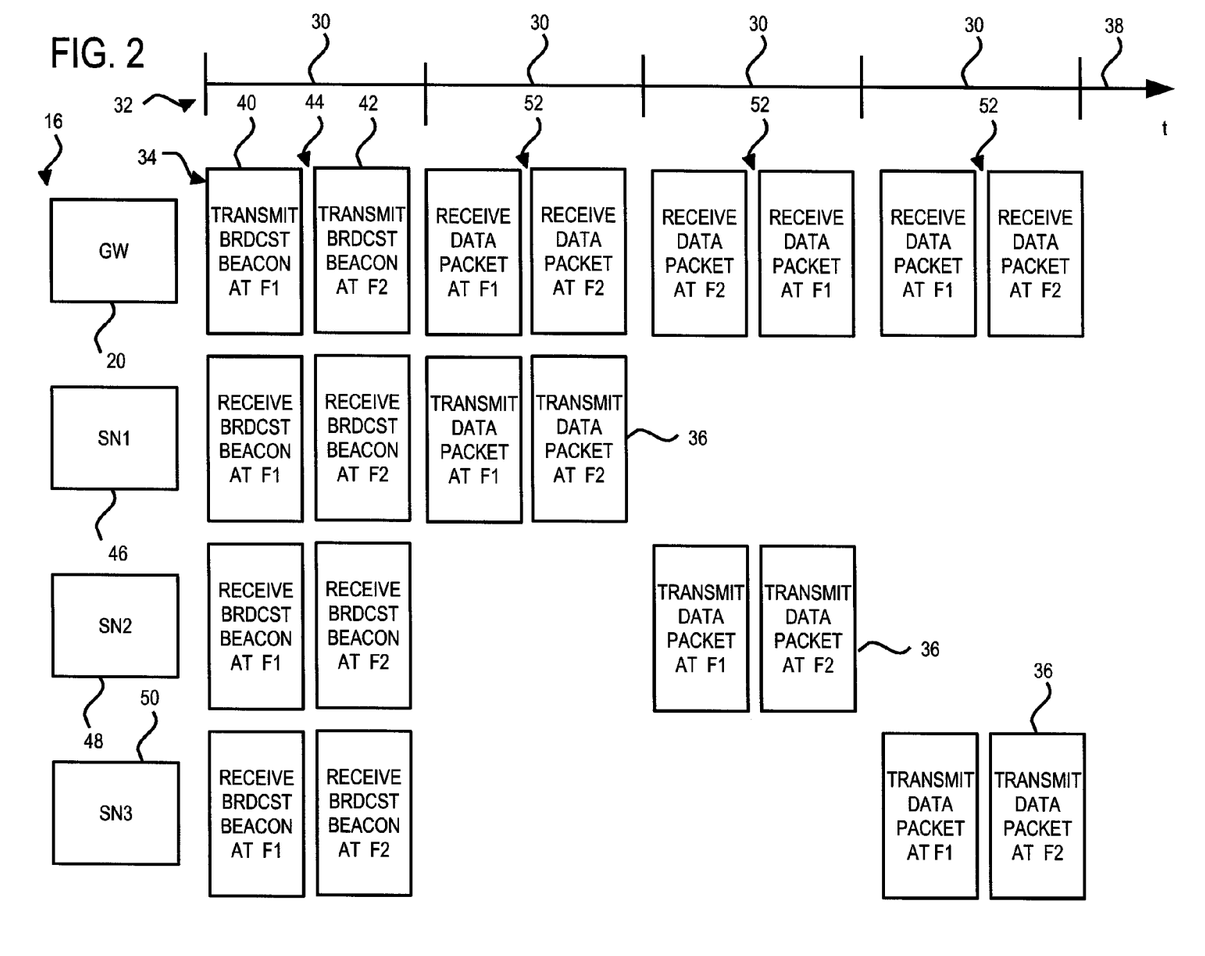
FIG. 2 is a graphical representation of a communications scheme useable with the system illustrated in FIG. 1.

Referring now to FIG. 2, a wireless communications scheme between the gateway device 20 and the plurality of wireless sensors 16 is shown. The plurality of wireless sensors 16 are associated with the gateway device 20 such that the gateway device assigns each of the sensors a specific time slot 30 for data exchange on the wireless communication link. Communication between gateway device 20 and wireless sensors 16 is divided into communication frames 32 (i.e., operative frames) containing a plurality of slots 30, similar to a TDMA-type system. One such communication frame 32 is shown in FIG. 2. The gateway device 20 may adjust frame 32 timing based upon the type of wireless sensor added to the NAP 10 (shown in FIG. 1). Based upon sensor data bandwidth, the gateway device 20 may expand or reduce the frame timing, slot widths and/or and number of slots. As an alternative to channels based on frequency, channels based on spreading codes, hopping patterns, or any other separation means of RF time-bandwidth product may also be used.

Several tasks are completed during each communication frame 32, including network management and sensor data exchange. At the start of each frame, the gateway device 20 forwards network information to each of the wireless sensors 16 using a broadcast beacon message 34 (i.e., activation signal) that is transmitted to, and received by, the wireless sensors 16. The beacon message 34 may include information as to future frequency channels to use, time to next beacon, etc. A time division multiple access (TDMA) type scheme is employed, such that gateway device 20 transmits the beacon message 34 at a fixed interval, thus defining a plurality of communication frames 32. The wireless sensors 16 associated with the gateway device 20 awaken from a lower power state upon reception of the beacon message 34. Each sensor 16 then waits in a low power consumption state until its assigned time slot 30 within the communication frame 32 that it is associated with occurs. During their assigned time slots within the communication frame 32, each wireless sensor 16 transmits a data packet 36 containing data on the measured patient parameter to the gateway device 20. The data packet 36 includes at least patient data acquired during the present communication frame 32. It is also envisioned that data packet 36 can include patient data from an immediately preceding or previous communication frame, or from several preceding communication frames, so long as data latency issues are addressed. An association interval 38 then follows subsequent to communication of the data packet 36 from each of the associated wireless sensors to the gateway device 20 and prior to conclusion of the communication frame 32 in which any additional wireless sensors 16 that are to be added to the sensor network 18 (shown in FIG. 1) are assigned a respective slot 30. In one embodiment, the wireless sensors 16 sleep during this association period 38 and until the next beacon interval (i.e., next communication frame). At the end of communication frame 32, both gateway device 20 and wireless sensors 16 re-tune to a common frequency, in preparation for a subsequent communication frame.

In order to provide robustness to the wireless communication between gateway device 20 and wireless sensors 16, the beacon message 34 is transferred to the wireless sensors 16 multiple times, with each transmitted beacon message 34 containing the same data/instructions therein. While described herebelow as an initial beacon message 40 and a follow-up 42 beacon message (i.e., two messages), it is also envisioned that additional repeat beacon messages could be transmitted. The initial beacon message 40 is transmitted by gateway device 20 at a first frequency, F1 (i.e., over a first frequency channel). No acknowledgement of receipt of this initial beacon message 40 is generated by the wireless sensors 16. Thus, subsequent to the initial transmission, gateway device 20 automatically transmits a follow-up beacon message 42 at a second frequency, F2 (i.e., over a second frequency channel) different from the first frequency. In one embodiment, the first frequency and the second frequency differ by a pre-determined and fixed amount; however, it is also envisioned that the difference between the frequencies can be a pseudo-random difference that is generated by gateway device 20 (i.e., the micro-controller 24 shown in FIG. 1). The pseudo-random difference is limited within a certain frequency range consistent with frequencies commonly used for wireless RF communication.

As stated above, the initial beacon message 40 is transmitted to the wireless sensors 16 at a first frequency, F1. Wireless sensors 16, in an initial state, are tuned to the first frequency, so as to await receipt of the initial beacon message 40 from the gateway device 20. Wireless sensors 16 are programmed to await transmission of the initial beacon message 40 for a pre-determined time period 44. If no beacon message is received within this pre-determined time period 44, the wireless sensors 16 tune into (i.e., switch to) the second frequency and monitor for the follow-up beacon message 42 transmitted at the second frequency, F2. The transmission of the beacon message 34 at each of the first and the second frequencies helps to ensure receipt of the beacon message by the wireless sensors 16.

Upon receipt of the beacon message 34, at either the first or second transmission frequency, each of the wireless sensors 16 are activated to transmit a data packet 36 (containing acquired patient data) to the gateway device 20. Similar to transmission of the beacon message 34, the patient data is also transmitted multiple times sequentially and over differing frequencies. Again, while described here below as a pair of repeat data packets 36 transferred at first and second frequencies, it is envisioned that additional repeat data packets 36 could be transmitted, constrained only by the time length of the communication window and amount of messages transmittable during that length. No acknowledgement of receipt of the patient data is generated by the gateway device 20. Thus, subsequent to a first transmission of a data packet, a wireless sensor 16 can re-transmit the data packet 36 at a different frequency according to one of the patterns described in detail here below, and without having to wait for feedback as to whether the data packet 36 sent in the first transmission was successfully received. Elimination of an acknowledgement receipt reduces the time between subsequent, repeat transmissions, thus addressing issues relating to delay requirements/data latency.

The implementation of a certain communications scheme/pattern for varying the time and frequency of data packet 36 transmissions, as selected from the plurality of schemes/patterns described herebelow, is determined (at least in part) by the characteristics of the ambient radio environment and jammers present in the vicinity of an NAP 10 (shown in FIG. 1). That is, gateway device 20 can invoke a different time/frequency pattern for data packet 36 transmission based on known interfering systems in the vicinity, in order to try and improve performance in the presence of those interfering systems. In one embodiment, gateway device 20 is configured to sense the presence of other interfering systems through observance of an increase in packet errors (i.e., transmission failures, data within the packet disassociated from the measured parameter, etc.) and by sensing outside radio sensors (i.e., sensors outside the associated wireless sensors 16) during the association period 38. Selection of the appropriate communications scheme/pattern for optimizing data packet 36 transmission can therefore be determined by gateway device 20.

As described below, and for purposes of example, a sensor network in communication with the gateway device 20 is comprised of three wireless sensors 16, as shown in FIG. 2. In the embodiment shown in FIG. 2, a first sensor node 46, a second sensor node 48, and a third sensor node 50, are in wireless communication with gateway device 20 and transmit patient data thereto in sequential order via data packets 36. That is, the first sensor node 46, the second sensor node 48, and the third sensor node 50 transmit patient data according to the slot 30 within the communication frame 32 with which each node is associated. As shown in FIG. 2, the first sensor node 46 transmits data 36 in its associated slot at the first frequency and then at the second frequency. After the repeat transmission of a data packet 36 by first sensor node 46 at distinct first and second frequencies, the second sensor node 48 subsequently transmits a data packet 36 at the first frequency and then at the second frequency in its allotted slot 30. Following the transmissions by the second sensor node 48, the third sensor node 50 then subsequently transmits patient data at the first frequency and then at the second frequency in its assigned slot 30.

To accommodate receipt of the patient data, gateway device 20 is synchronized with the switching of the first, second, and third sensor nodes 46, 48, 50 between the first frequency and the second frequency. That is, gateway device 20 tunes alternately between the first frequency, F1, and the second frequency, F2, in a pattern that matches the transmission of data packets 36 from the first, second, and third sensor nodes 46, 48, 50 over the first frequency and the second frequency. Similar to that described above with respect to transmission of the beacon message 34, gateway device 20 is programmed to await transmission of a data packet 36 from a sensor node at a specified frequency, for a pre-determined time period 52. If no data packet 36 is received within this pre-determined time period 52 over the monitored frequency, the gateway device 20 tunes into (i.e., switches to) a second, different frequency and monitors for the data packet 36 transmitted at that second frequency. With respect to the embodiment shown in FIG. 2, this means that gateway device 20 will initially be tuned into the first frequency when awaiting a data packet 36 from each of the individual sensor nodes 46, 48, 50. The gateway device 20 will then tune to the second frequency if the data packet 36 from each sensor node, initially sent at the first frequency, is not received within the pre-determined time period 52. As described here below, however, it is also envisioned that the transmission of patient data can be modified to lessen the amount of frequency switching performed by the gateway device 20 to remain in synchronization with each transmission of patient data by the sensor nodes.

Figure 3:
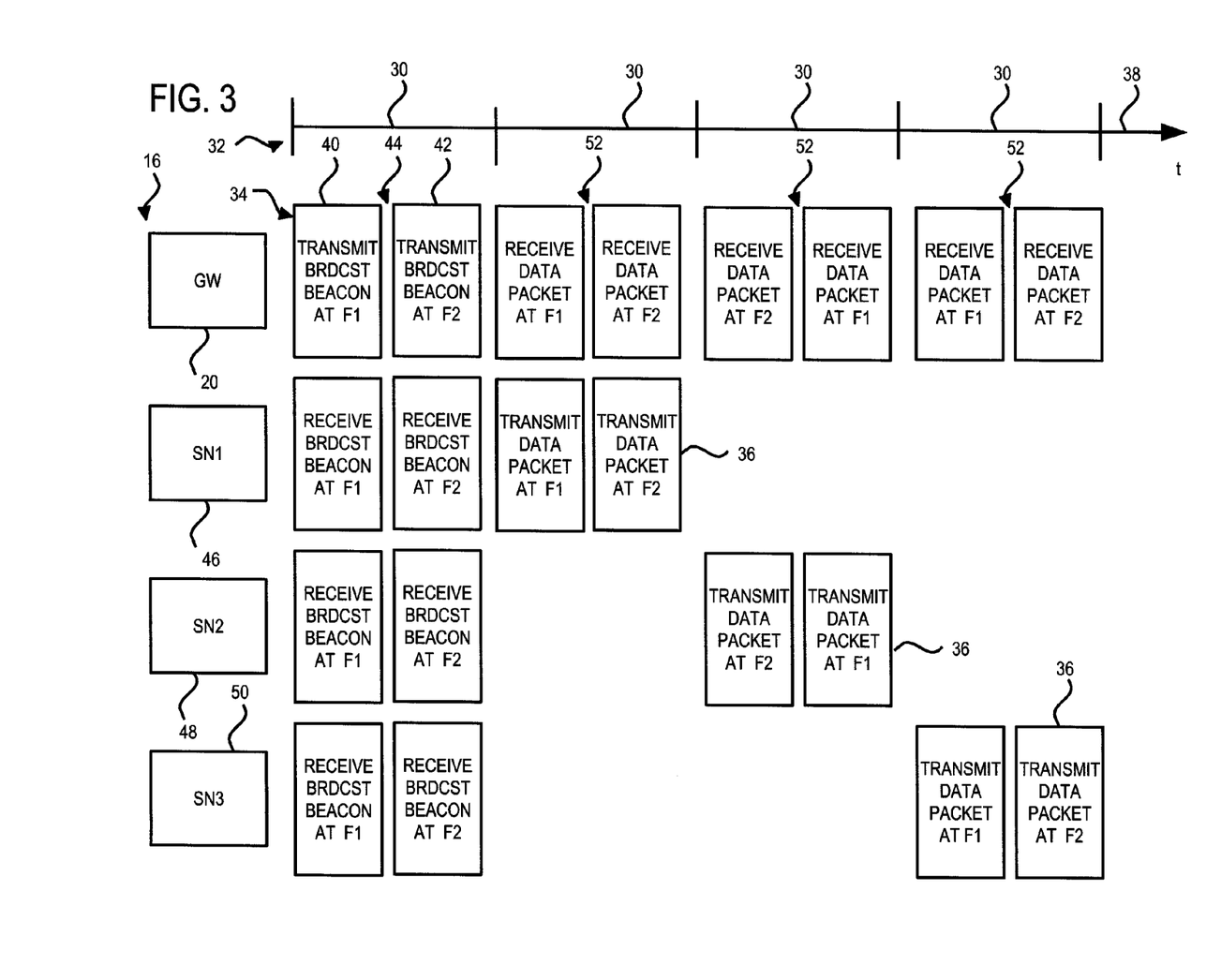
FIG. 3 is a graphical representation of another communications scheme useable with the system illustrated in FIG. 1.

Referring now to FIG. 3, in another embodiment of the invention, first sensor node 46, second sensor node 48, and third sensor node 50, are in wireless communication with gateway device 20 and transmit patient data packets 36 thereto in sequential order. That is, the first sensor node 46, the second sensor node 48, and the third sensor node 50 transmit data packets 36 according to the slot 30 within the communication frame 32 with which each node is associated. As shown in FIG. 3, the first sensor node 46 transmits data packets 36 in its associated slot at the first frequency and then at the second frequency. After the repeat transmission of a data packet 36 by first sensor node 46 at distinct first and second frequencies, the second sensor node 48 subsequently transmits data packets 36 at the second frequency and then at the first frequency in its allotted slot 30. As this initial transmission by second sensor node 48 of data packet 36 at the second frequency immediately follows a transmission by the first sensor node 46 at that second frequency, gateway device 20 remains tuned to the second frequency when transitioning between slots 30 from the first sensor node 46 to the second sensor node 48. In a similar fashion, following the transmissions by the second sensor node 48, the third sensor node 50 subsequently transmits patient data initially at the first frequency and then at the second frequency. Thus again, gateway device 20 is able to remain tuned to the first frequency when transitioning from the second sensor node 48 to the third sensor node 50. The amount of frequency tuning and frequency switching required by gateway device 20 to remain in synchronization with each transmission of data packets 36 by the sensor nodes 46, 48, 50 is thus reduced in the embodiment shown in FIG. 3.

Figure 4:
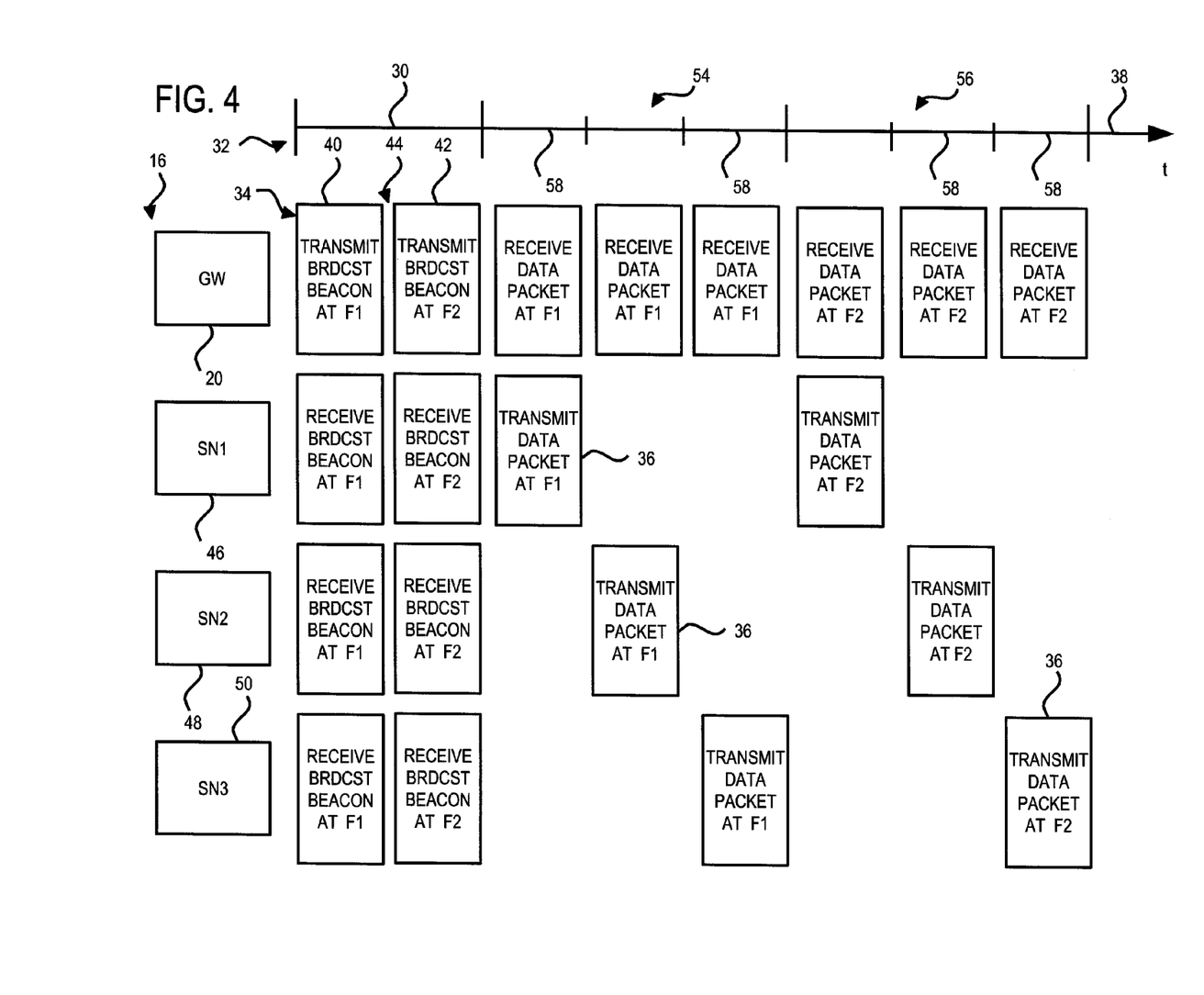
FIG. 4 is a graphical representation of another communications scheme useable with the system illustrated in FIG. 1.

Referring now to FIG. 4, in another embodiment, each communication frame 32 is divided into a plurality of defined sub-frames 54, 56. As shown in FIG. 4, communication frame 32 is further comprised of a first sub-frame 54 and a second sub-frame 56, with each sub-frame containing an identical number of slots 58. Each sensor node corresponds to an identical slot 58 in each sub-frame (i.e., first sensor node 46 transmits in the first slot of each of the first and second sub-frames). Transmission of patient data via data packets 36 from the plurality of wireless sensors 16 in the sensor network 18 (shown in FIG. 1) is divided between the two sub-frames. That is, as shown in FIG. 4, each of a first sensor node 46, a second sensor node 48, and a third sensor node 50 are programmed to transmit a data packet 36 at a first frequency during the first sub-frame 54. The transmission of data packets 36 by each sensor is ordered according to each sensor's associated time slot 58 within the first sub-frame 54. Upon completion of the first sub-frame 54, the second sub-frame 56 is entered, during which each of first sensor node 46, second sensor node 48, and third sensor node 50 are programmed to re-transmit their respective data packets 36 at a second, distinct frequency. Similar to transmission during the first sub-frame 54, the transmission of data packets 36 by each sensor in the second sub-frame 56 is again ordered according to each sensor's associated time slot 58 within the second sub-frame 56.

Division of the communication frame into first and second sub-frames 54, 56, as described above, allows for prolonged periods of patient data transmission at a specified frequency. That is, all data packets 36 transmitted by the sensor nodes 46, 48, 50 in the first sub-frame 54 are transmitted at the first frequency. Thereafter, all the data packets 36 that are re-transmitted by the sensor nodes in the second sub-frame 56 are transmitted at the second frequency. Such a transmission protocol allows gateway device 20 to remain tuned to a single frequency for the entirety of a sub-frame before having to retune to a different frequency. A reduction in the number of re-tunings required by gateway device 20 to remain synchronized with sensor node transmissions reduces energy consumption as well as eliminates time delays associated with re-tuning.

While each of a plurality of transmission patterns for the beacon message 34 and the patient data packets 36 have been set forth separately here above, it is envisioned that the transmission patterns can be used in conjunction with one another. That is, the transmission pattern employed for data transfer between the gateway device 20 and the plurality of wireless sensors 16 can be varied between successive communication frames 32. Such variance in transmission patterns can yield still further improved and robust wireless communication, as the transmission patterns can be varied according to the duty cycle of any interfering radio transmissions to avoid interference therewith.

In another embodiment, frequency agility/hopping is employed by gateway device 20 between communication frames 32 to select available radio channels (e.g., among a 2.4 GHz ISM band) which are not used by other gateways or other radio systems. That is, gateway device 20 (by way of supervisor gateway 29 shown in FIG. 1) commands transmission frequencies used in a subsequent communication frame 32 during its beacon message 34 to alter at least one of the frequencies transmitted by the gateway device 20 and wireless sensors 16 to a previously unused frequency. The additional frequency hopping employed between communication frames 32 further ensures that transmission of beacon message 34 and data packets 36 in the NAP 10 (shown in FIG. 1) is successful by further increasing the variability of the transmissions. The gateway device 20 may also broadcast a set of frequency patterns for future communications.

Therefore, according to one embodiment of the present invention, a wireless patient monitoring system includes a plurality of sensor nodes configured to acquire patient data from a patient and a gateway device in bi-directional wireless communication with the plurality of sensor nodes for a plurality of defined communication frames. The gateway device is configured to transmit a beacon message to the plurality of sensor nodes at each of a plurality of frequencies. The plurality of sensor nodes is further configured to receive the beacon message from the gateway device and transmit the acquired patient data to the gateway device at each of the plurality of frequencies.

According to another embodiment of the present invention, a method for patient monitoring includes the steps of arranging a plurality of wireless sensors on a patient to acquire health data therefrom and associating the plurality of wireless sensors with a gateway controller by assigning each of the plurality of wireless sensors to a timeslot within the operative frame. The method also includes the steps of transmitting a beacon signal from the gateway controller to the plurality of wireless sensors to activate the wireless sensors during an operative frame and transmitting the health data from the plurality of wireless sensors to the gateway controller via a plurality of data packets during the operative frame in response to the beacon signal. At least one of the beacon signal and the data packets are transmitted over a first frequency channel and a second frequency channel during the operative frame.

According to yet another embodiment of the present invention, a wireless sensor communications system includes a sensor network configured to acquire system data from a monitored system and a controller positioned in proximity to the sensor network and in wireless communication therewith. Each of the sensor network and the controller are configured to sequentially transmit and receive wireless signals over a first frequency channel (F1) and over a second frequency channel (F2) and switch between the first frequency channel and the second frequency channel at least once during each of a plurality of communication frames, the wireless signals including an activation signal and system data.

The present invention has been described in terms of the preferred embodiment, and it is recognized that equivalents, alternatives, and modifications, aside from those expressly stated, are possible and within the scope of the appending claims.

What is claimed is:

1. A wireless patient monitoring system comprising:
    a plurality of sensor nodes configured to acquire patient data from a patient; and
    a gateway device in bi-directional wireless communication with the plurality of sensor nodes for a plurality of defined communication frames, the gateway device configured to transmit a beacon signal to each of the plurality of sensor nodes at each of a plurality of frequencies; and
    wherein each of the plurality of sensor nodes are further configured to:
        receive the beacon signal from the gateway device; and
        transmit the acquired patient data to the gateway device at each of the plurality of frequencies;
    wherein the plurality of frequencies comprises a first frequency and a second frequency and the plurality of sensor nodes are further configured to tune to the first frequency to receive the beacon signal and tune to the second frequency if the beacon signal transmitted at the first frequency is not received within a pre-determined time limit; and
    wherein the gateway device is further configured to tune to the first frequency to receive the patient data and, if the patient data is not received within a pre-determined time limit, tune to the second frequency.

2. The wireless patient monitoring system of claim 1 wherein each of the gateway device and the plurality of sensor nodes are configured to retune to the first frequency at the end of each of the plurality of defined communication frames.

3. The wireless patient monitoring system of claim 1 wherein the first frequency and the second frequency are offset by one of a pre-determined fixed amount and a pseudo-random amount.

4. The wireless patient monitoring system of claim 1 further comprising a supervisor gateway to control the gateway device, the supervisor gateway device configured to cause the gateway device to shift at least one of the first frequency and the second frequency by a pre-determined amount between a first communication frame and a subsequent communication frame.

5. The wireless patient monitoring system of claim 1 wherein the plurality of sensor nodes further comprises at least a first sensor node and a second sensor node, the first sensor node and the second sensor node transmitting patient data in sequential order during each of the defined communication frames.

6. The wireless patient monitoring system of claim 5 wherein the first sensor node transmits patient data at the first frequency and then at the second frequency, the second sensor node subsequently transmits patient data at the first frequency and then at the second frequency, and any additional sensor nodes in the plurality of sensor nodes subsequently transmit patient data at the first frequency and then at the second frequency, and wherein the gateway device is synchronized with the switching between the first frequency and the second frequency of each of the sensor nodes.

7. The wireless patient monitoring system of claim 5 wherein the first sensor node transmits patient data at the first frequency and then at the second frequency, the second sensor node subsequently transmits patient data at the second frequency and then at the first frequency, and any additional sensor nodes in the plurality of sensor nodes subsequently transmit patient data at the first frequency and the second frequency in an opposite order from a previous sensor in the plurality of sensors, and wherein the gateway device is synchronized with the switching between the first frequency and the second frequency.

8. The wireless patient monitoring system of claim 1 wherein each of the plurality of defined communication frames further comprises a first sub-frame and a second sub-frame, and wherein each of the plurality of sensor nodes transmits patient data at the first frequency during the first sub-frame and transmits patient data at the second frequency during the second sub-frame.

9. The wireless patient monitoring system of claim 1 wherein each of the gateway device and the at least one sensor node comprises:
    an integrated circuit radio transceiver to transmit and receive wireless signals at the first frequency and the second frequency; and
    a micro-controller configured to switch the integrated circuit radio transceiver between transmission of the wireless signals at the first frequency and the second frequency and switch the integrated circuit radio transceiver between reception of the wireless signals at the first frequency and the second frequency.

10. The wireless patient monitoring system of claim 1 wherein the at least one sensor node comprises a wireless body worn sensor.

11. The wireless patient monitoring system of claim 1 wherein the gateway device comprises a wireless body worn device.

12. The wireless patient monitoring system of claim 1 wherein the gateway device is further configured to transmit information identifying available frequencies.

13. A method for patient monitoring, comprising:
arranging a plurality of wireless sensors on a patient to acquire health data therefrom during an operative frame;
associating the plurality of wireless sensors with a gateway controller by assigning each of the plurality of wireless sensors to a timeslot within the operative frame;
transmitting a beacon signal from the gateway controller to the plurality of wireless sensors to activate the wireless sensors during an operative frame;
transmitting the health data from the plurality of wireless sensors to the gateway controller via a plurality of data packets during the operative frame in response to the beacon signal; and
sequentially transmitting data packets at the first frequency and then at the second frequency within a first timeslot;
wherein at least one of the beacon signal and the data packets are transmitted over a first frequency channel and a second frequency channel during the operative frame;
wherein the step of transmitting the health data comprises:
in each subsequent timeslot, sequentially transmitting the first and second frequencies in a reverse order from an immediately preceding timeslot.

14. The method of claim 13 further comprising the steps of shifting at least one of the first frequency channel and the second frequency channel by a pre-determined amount between a first operative frame and a subsequent operative frame.

15. The method of claim 13 further comprising:
transmitting information identifying available frequencies from the gateway controller to the wireless sensors.

16. A method for patient monitoring, comprising:
arranging a plurality of wireless sensors on a patient to acquire health data therefrom during an operative frame;
associating the plurality of wireless sensors with a gateway controller by assigning each of the plurality of wireless sensors to a timeslot within the operative frame;
transmitting a beacon signal from the gateway controller to the plurality of wireless sensors to activate the wireless sensors during an operative frame;
transmitting the health data from the plurality of wireless sensors to the gateway controller via a plurality of data packets during the operative frame in response to the beacon signal; and
wherein at least one of the beacon signal and the data packets are transmitted over a first frequency channel and a second frequency channel during the operative frame;
wherein the step of transmitting the health data comprises:
sequentially transmitting the data packets from the plurality of wireless sensors during a first sub-frame within the operative frame and over the first frequency channel; and
sequentially transmitting the data packets from the plurality of wireless sensors during a second sub-frame within the operative frame and over the second frequency channel, the second sub-frame falling after the first sub-frame within the operative frame.

17. A method for patient monitoring, comprising:
arranging a plurality of wireless sensors on a patient to acquire health data therefrom during an operative frame;
associating the plurality of wireless sensors with a gateway controller by assigning each of the plurality of wireless sensors to a timeslot within the operative frame;
transmitting a beacon signal from the gateway controller to the plurality of wireless sensors to activate the wireless sensors during an operative frame;
transmitting the health data from the plurality of wireless sensors to the gateway controller via a plurality of data packets during the operative frame in response to the beacon signal;
tuning the plurality of wireless sensors to receive the beacon signal transmitted over the first frequency channel; and
tuning the plurality of wireless sensors to receive the beacon signal transmitted over the second frequency channel if the beacon signal transmitted over the first frequency channel is not received within a pre-determined time limit;
wherein at least one of the beacon signal and the data packets are transmitted over a first frequency channel and a second frequency channel during the operative frame.

18. A method for patient monitoring, comprising:
arranging a plurality of wireless sensors on a patient to acquire health data therefrom during an operative frame;
associating the plurality of wireless sensors with a gateway controller by assigning each of the plurality of wireless sensors to a timeslot within the operative frame;
transmitting a beacon signal from the gateway controller to the plurality of wireless sensors to activate the wireless sensors during an operative frame;
transmitting the health data from the plurality of wireless sensors to the gateway controller via a plurality of data packets during the operative frame in response to the beacon signal;
tuning the gateway controller to receive the data packets transmitted over the first frequency channel; and
tuning the gateway controller to receive the data packets transmitted over the second frequency channel if the data packets transmitted over the first frequency channel are not received within a pre-determined time limit;
wherein at least one of the beacon signal and the data packets are transmitted over a first frequency channel and a second frequency channel during the operative frame.

19. A wireless sensor communications system comprising:
a wireless sensor network configured to acquire system data from a monitored system;
a controller positioned in proximity to the sensor network and in wireless communication therewith;
wherein each of the sensor network and the controller are configured to sequentially transmit and receive wireless signals over a first frequency channel (F1) and over a second frequency channel (F2) and switch between the first frequency channel and the second frequency channel at least once during each of a plurality of communication frames, the wireless finals including an activation signal and system data; and,
wherein the wireless sensor network is further configured to:
tune to F1 to receive the activation signal;
tune to F2 to receive the activation signal if the activation signal transmitted over F1 is not received within a pre-determined time limit; and
transmit the system data to the controller over each of F1 and F2 upon receipt of the activation signal.

20. The wireless sensor communications system of claim 19 wherein the wireless sensor network further comprises a plurality of sensor nodes, and wherein the plurality of sensor nodes are configured to transmit the system data to the controller within each of the plurality of communication frames in at least one of the following representative sequences:

(A) a first sensor transmitting at F1 then F2, a second sensor subsequently transmitting at F1 then F2, and all remaining sensors in the plurality of sensors subsequently transmitting at F1 then F2;

(B) a first sensor transmitting at F1 then F2, a second sensor subsequently transmitting at F2 then F1, and all remaining sensors in the plurality of sensors subsequently transmitting F1 and F2 in an opposite pattern from a previous sensor in the plurality of sensors; and (C) all sensors in the plurality of sensors sequentially transmitting at F1 and then all sensors in the plurality of sensors sequentially transmitting at F2, the F1 transmissions occurring during a first sub-frame and the F2 transmissions occurring during a second sub-frame.

21. The wireless sensor communications system of claim 20 wherein the controller is configured to select one of the representative transmission sequences based on at least one of observation of data packet errors and sensing of outside radio sensors.

22. The wireless sensor communications system of claim 19 wherein the wireless sensor network comprises a body worn patient sensor network configured to acquire health data from a patient.

23. The wireless sensor communications systems of claim 19 wherein the controller is further configured to transmit information identifying available frequencies.

* * * * *